United States Patent
Dettinger et al.

(10) Patent No.: US 10,706,485 B2
(45) Date of Patent: Jul. 7, 2020

(54) CREATING INDIVIDUALLY TAILORED CARE PLANS

(71) Applicant: PREVENTICE, INC., Rochester, MN (US)

(72) Inventors: Richard D. Dettinger, Rochester, MN (US); Richard M. Smith, Oronoco, MN (US); Scott J. Burrichter, Rochester, MN (US)

(73) Assignee: Preventice Solutions, Inc., Rochester, MN (US)

( * ) Notice: Subject to any disclaimer, the term of this patent is extended or adjusted under 35 U.S.C. 154(b) by 642 days.

(21) Appl. No.: 14/490,413

(22) Filed: Sep. 18, 2014

(65) Prior Publication Data

US 2016/0086297 A1 Mar. 24, 2016

(51) Int. Cl.
*G06Q 50/20* (2012.01)
*G06Q 50/24* (2012.01)
(Continued)

(52) U.S. Cl.
CPC ......... *G06Q 50/24* (2013.01); *G06F 19/3418* (2013.01); *G06Q 10/101* (2013.01); *G16H 10/60* (2018.01)

(58) Field of Classification Search
CPC ........ G06F 19/322; G06F 17/30; G06F 19/30; G06F 19/32; G06F 19/321; G06F 19/324;
(Continued)

(56) References Cited

U.S. PATENT DOCUMENTS

| 5,786,816 A | * | 7/1998 | Macrae | G06F 19/325 128/920 |
| 5,933,136 A | * | 8/1999 | Brown | G06F 19/3418 715/741 |

(Continued)

FOREIGN PATENT DOCUMENTS

WO 2014/116968 A1 7/2014

OTHER PUBLICATIONS

International Search Report and Written Opinion for corresponding International Application No. PCT/US2015/050563, dated Nov. 12, 2015 (13 pages).

*Primary Examiner* — Michael Tomaszewski
(74) *Attorney, Agent, or Firm* — Patterson + Sheridan, LLP

(57) ABSTRACT

Embodiments presented herein describe techniques for generating a care plan tailored for an individual. According to one embodiment of the present disclosure, a care platform receives a selection of one or more care protocol templates to assign to a patient. Each care protocol template is associated with a medical condition to be treated. The care platform generates tasks to be performed by the patient, observation metrics specifying types of patient biometrics to monitor, and thresholds associated with each selection. The care platform receives one or more customizations to the tasks, observation metrics, and thresholds and determines whether any of the tasks or the customizations to the tasks conflict with one another. Upon identifying one or more conflicts, the conflicts are resolved based on specified rules associated with each conflicting task. The care plan is generated based on the observation metrics, thresholds, customizations, and resolved tasks.

19 Claims, 7 Drawing Sheets

(51) Int. Cl.
*G06F 19/00* (2018.01)
*G16H 10/60* (2018.01)
*G06Q 10/10* (2012.01)

(58) Field of Classification Search
CPC .... G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 50/22; G06Q 50/24; G06Q 40/08; G06Q 10/10; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00

See application file for complete search history.

(56) References Cited

U.S. PATENT DOCUMENTS

| | | | |
|---|---|---|---|
| 2002/0019749 A1* | 2/2002 | Becker | G06F 19/325 705/2 |
| 2006/0287885 A1* | 12/2006 | Frick | A61B 5/00 705/2 |
| 2010/0179825 A1* | 7/2010 | Hanov | G06F 19/325 705/2 |
| 2012/0221352 A1* | 8/2012 | Georgeff | G16H 50/20 705/2 |
| 2013/0179178 A1* | 7/2013 | Vemireddy | G06Q 10/00 705/2 |

* cited by examiner

/Interface/

Patient Name: 305 Doe, John    Patient ID: 310 1-12345-678

Care Protocol: 315 ▶ High Blood Pressure

Protocol Duration
320 30 Days
Select Phase: 325
▶ Phase I 330

Tasks: 335
▶ Walk 10 minutes

Edit    Remove    Add

Cancel    Save

/Interface/ — 400

Patient Name: Doe, John — 405
Patient ID: 1-12345-678 — 410
Condition: High Blood Pressure — 415

Task | Frequency
--- | ---
Wear sensor | As directed
Take blood pressure | Once a day
Take 60 milligrams of aspirin | Every morning

420 / 425

Threshold Set 1: Weekly Weight — 430

| Type | Value | Warning Level | Symptoms | Alert Type | Delete |
| --- | --- | --- | --- | --- | --- |
| Gain | 2.5 kg | Tier 2 | Multiple symptoms selected | Chart | X |
| Loss | 2.5 kg | Tier 1 | Any | Chart | X |

Add

Threshold Set 2: Daily Blood Pressure

| Type | Value | Warning Level | Symptoms | Alert Type | Delete |
| --- | --- | --- | --- | --- | --- |
| Not received | --- | Tier 3 | Any | Call | X |
| Less than | < 90 | Tier 2 | None | Chart | X |
| Greater than | > 120 | Tier 2 | Racing heart, light headed | Chart | X |

Add

Add Threshold Set        Cancel    Save

Figure 4

CREATING INDIVIDUALLY TAILORED CARE PLANS

BACKGROUND

Field

Embodiments presented herein generally describe techniques related to health care, and more specifically, for generating an individualized care plan for a patient.

Description of the Related Art

In the health care field, a care plan is a set of tasks provided by a health care practitioner (e.g., a doctor) to a patient. Historically, such a care plan is a written document that provides directions and routines for the patient to follow to manage certain health conditions. The care plan may include a set of tasks (e.g., exercise for a given duration) for the patient to perform, content that educates the patient about a diagnosed condition (e.g., brochures describing the diagnosed condition), and logs for the patient to periodically record information in (e.g., weight, blood pressure, etc.). As an example, a doctor might create a care plan for a patient with hypertension that includes several brochures describing hypertension and hypertension treatment and assigned tasks such as walking on a treadmill for thirty minutes each morning, drinking a glass of water every three hours, and recording blood pressure at the end of each day. Thus, as part of the treatment of the condition, the patient is expected to adhere to the tasks listed in the care plan and to then follow up with the doctor in a subsequent appointment to assess the patient's progress.

The current care plan approach has several shortcomings. For instance, a care plan for a particular condition is often tailored towards the condition itself, without considering relevant details about a patient. Typically, once a doctor has diagnosed a patient with a particular condition, the doctor prints out a "one size fits all" care plan for the individual that instructs the individual on how to manage the condition. Although the doctor may include notes in the printed pamphlet describing the care plan, the doctor is often unable to modify the care plan otherwise (e.g., to craft the care plan specifically for the patient). Further, the doctor often has no way of determining the patient's adherence to the care plan until a follow-up appointment. Currently, to address this concern, care providers employ call centers to contact the patient periodically and determine whether the patient is following the care plan, but such an approach is costly and further exposes a patient's condition to more individuals than necessary.

SUMMARY

One embodiment provides a method for generating a care plan that describes an overall treatment regimen for a patient. The method generally includes receiving, via a processor, a selection of one or more care protocol templates to assign to the patient. Each selected care protocol template is associated with a treatment regimen for a corresponding medical condition. A care plan is generated based on each of the selected care protocol templates. The care plan includes a plurality of items associated with each of the selected care protocol templates. The method also includes applying a received customization to at least one of the plurality of items in the care plan. Upon identifying one or more conflicts between items in the plurality of items, the conflicts are resolved based on rules specified in each care protocol template associated with each conflicting item. The care plan is transmitted to a client device of the patient, wherein the client device is configured to configure one or more sensor devices to monitor the patient in accordance with the care plan.

Still another embodiment includes a computer-readable storage medium storing instructions, which, when executed on a processor, perform an operation for generating a care plan that describes an overall treatment regimen for a patient. The operation itself includes receiving, via a processor, a selection of one or more care protocol templates to assign to the patient. Each selected care protocol template is associated with a treatment regimen for a corresponding medical condition. A care plan is generated based on each of the selected care protocol templates. The care plan includes a plurality of items associated with each of the selected care protocol templates. The operation also includes applying a received customization to at least one of the plurality of items in the care plan. Upon identifying one or more conflicts between items in the plurality of items, the conflicts are resolved based on rules specified in each care protocol template associated with each conflicting item. The care plan is transmitted to a client device of the patient, wherein the client device is configured to configure one or more sensor devices to monitor the patient in accordance with the care plan.

Still another embodiment includes a system having a processor and a memory a memory storing one or more application programs configured to perform an operation for generating a care plan that describes an overall treatment regimen for a patient. The operation itself includes receiving a selection of one or more care protocol templates to assign to the patient. Each selected care protocol template is associated with a treatment regimen for a corresponding medical condition. A care plan is generated based on each of the selected care protocol templates. The care plan includes a plurality of items associated with each of the selected care protocol templates. The operation also includes applying a received customization to at least one of the plurality of items in the care plan. Upon identifying one or more conflicts between items in the plurality of items, the conflicts are resolved based on rules specified in each care protocol template associated with each conflicting item. The care plan is transmitted to a client device of the patient, wherein the client device is configured to configure one or more sensor devices to monitor the patient in accordance with the care plan.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 3 illustrates an example care protocol template, according to one embodiment.

FIG. 4 illustrates a task view of the care protocol template described in FIG. 3, according to one embodiment.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
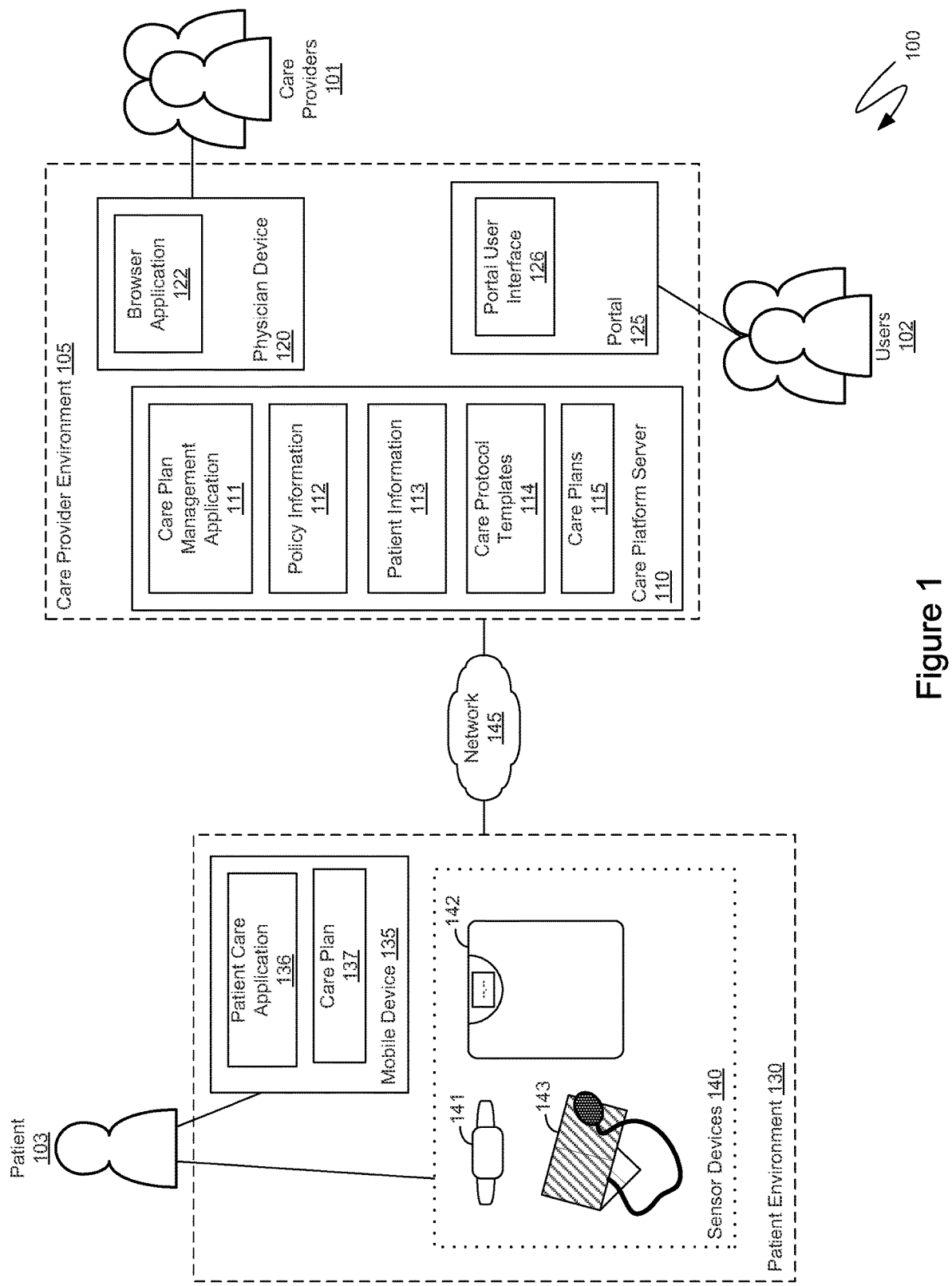
FIG. 1 illustrates an example computing environment, according to one embodiment.

Current approaches for providing a care plan to a patient are rigid. For example, in many cases, a physician who has diagnosed a patient with a particular condition may provide the patient with a generalized care plan commonly used to address that condition. Frequently, these generalized care plans are pre-printed documents that are not tailored to any particular patient but rather generally address the diagnosed medical condition. As a result, such printed care plans do not allow the physician to customize the care plan beyond annotating the care plan along the physical and behavioral margins. Such an approach is inconvenient when the physician must address multiple conditions through a care plan. Further, to address multiple conditions, a physician typically has to print separate care protocol pamphlets addressing each of multiple medical conditions the patient has been diagnosed with. Because some tasks in each of the printed pamphlets may overlap (e.g., two different care plans may instruct a patient to take a certain dosage of aspirin at a given time of day), a patient may have difficulty understanding the tasks to perform, leading to poor compliance. Moreover, in some situations, the tasks for treating the various diagnosed conditions may conflict with one another, leaving the patient unsure as to how to reconcile the conflict.

Embodiments presented herein describe techniques for generating a customized health care plan for an individual. In one embodiment, a care platform is provided that allows a physician to design a care plan tailored specifically for an individual patient. The care plan may include multiple care plan protocols, with each of the care plan protocols addressing a respective medical condition the patient has been diagnosed with. Generally, a care plan protocol describes the treatment of a particular medical condition. For instance, a care plan could specify a set of specific tasks for a patient to follow to manage the particular medical condition and could divide the tasks by phases and schedules. Generally, different care plan protocols may be available for each of a variety of conditions, such as congestive heart failure, diabetes, sprained ankle, etc. In addition, the care protocol may specify metrics that the care platform monitors during the patient's treatment, thresholds to detect for each metric, and remedial actions to be taken in response to detecting such thresholds. One example metric is blood pressure. The blood pressure metric may be associated with thresholds indicating values and conditions in which the care platform performs some action in response to detecting such values and conditions, e.g., sending instructions to the patient to rest for a given period of time. Further, the care protocol may provide the patient with resources to educate the patient about a diagnosed condition, treatment, and the like (e.g., instructional videos, articles, etc.).

A physician may assign multiple care plan protocols to a patient suffering from multiple medical conditions. To do so, the physician may configure templates for care plan protocols corresponding to the patient's conditions. Each care protocol template provides a general set of tasks to follow for a given condition. In one embodiment, the physician may configure the protocols for a specific patient via a user interface provided by the care platform. For example, assume a care protocol template for congestive heart failure recovery specifies a number of tasks to be performed at a specified interval (e.g., daily), such as walk for fifteen minutes, take prescribed medicine, record blood pressure, and record weight. If the physician deems that the patient is already within a healthy weight, the physician may remove the "record weight" task from the protocol. Further, the physician may also adjust the length of time that the patient should walk. In addition, the physician may insert additional tasks to the protocol.

Further, the physician may customize metrics specified in the care protocol and thresholds associated with each metric. Continuing the example of a care protocol for congestive heart failure recovery, the care protocol may specify a heart rate metric as well as a threshold that alerts the physician whenever the patient's heart rate is over a value X. In such a case, the physician may adjust the threshold, such as by adding conditions that need to be satisfied before alerting the physician, e.g., in order to trigger an alert due to the patient's heart rate being above a value X, the patient's activity level must be below a value Y.

The care platform may consolidate the configured care plan protocols into one overall care plan for the patient. However, it is possible that some tasks and phases of different care plan protocols overlap. As such, the care platform may perform operations to reconcile any conflicts between care plan protocols as part of the care plan creation. For example, a care plan protocol for high blood pressure and another for diabetes may include a step for walking for ten minutes each day. Both protocols may also include a step for taking two aspirin pills in the morning, and including two separate steps for taking aspirin may yield unintended consequences related to a dosage that the patient should be taking. As such, the care platform could consolidate the two separate tasks into a single task of taking two aspirin pills each morning.

In one embodiment, each task and threshold in a care plan protocol has an associated conflict resolution rule that the care platform evaluates when consolidating protocols. The conflict resolution rule may specify whether and how a given task (or threshold) may be merged with overlapping tasks (or thresholds) in other protocols. For example, the care platform may specify that tasks requiring a patient to take medication should be merged with other tasks involving the same medication. In addition, the conflict resolution rule may specify whether two or more overlapping tasks should be performed in separately. Further, the care platform may reconcile similar tasks that occur at different periods of the day based on the conflict resolution rules for each task. For example, a task for a congestive heart failure protocol may instruct the patient to take a dosage of aspirin in the morning, where another task for a sprained ankle protocol may instruct the patient to take a dosage of aspirin in the evening. Moreover, each of the care plan protocols could further specify that while a daily aspirin dosage of a particular amount is needed, the timing of the daily dosage is flexible. As such, the care platform could resolve the timing conflict between the two exemplary care protocols by specifying that only a daily dosage of the particular amount of aspirin should be taken. In other situations, the care protocols could specify conflict resolution rules for each task which indicate that both tasks may be included in the same care plan.

Once created, the care platform may transmit the care plan to an application in a device owned by the patient, e.g., a smart phone or tablet device. Though the device, the patient may access the care plan and understand the tasks to perform. Further, the application may receive information from various sensors that monitor patient activity (e.g., heart rate, weight, blood pressure). The application can record the information to the care plan and relay information to the care platform. As a result, the physician (or members of the patient's care team such as caregivers) can monitor the patient's adherence to the care plan.

In one embodiment, each task set out in the care plan may be associated with an observation threshold, such that when patient activity reaches a particular threshold, the care platform may take a certain action in response, such as notifying the physician. Another example of an action that the care plan may take is prompting the patient to report symptoms via the mobile device. Input from the patient may be used to assist the care platform in interpreting metrics and determining whether to escalate care. That is, symptoms reported by the patient may be included as a threshold condition, such that if particular symptoms are noted in combination with given metrics, the care platform may take further action, such as by including additional tasks to reorient observed metrics to an acceptable level or by alerting a physician or emergency services.

Moreover, the care plan could perform treatment operations responsive to detecting an observation metric that exceeds a threshold value, before escalating to a physician or emergency services. For example, upon detecting the patient's heart rate exceeds a threshold value while the patient's overall activity level is relatively low, the care platform could present the patient with instructions (e.g., via the mobile device) to sit and rest for a period of time. If the patient's heart rate remains elevated after the patient has complied with the instructions, the care platform could then determine that more urgent treatment is needed and could alert emergency services as to the patient's condition. As stated, the physician may create, edit, or remove observation thresholds while configuring a care protocol template. For example, for a task that requires a patient to record a daily weight, the physician may specify a threshold weight gain at which to generate an alert, e.g., if the patient gains two pounds after a day.

FIG. 1 illustrates an example computing environment 100, according to one embodiment. As shown, the computing environment 100 may include a care provider environment 105 and a patient environment 130, each connected to one another via a network 145. The environments 105 and 130 allow a patient 103 to communicate with a care provider 101 (e.g., a physician).

The care provider environment 105 includes a care platform server 110, a physician device 120, and a portal 125. Each of the care platform server 110, physician device 120, and portal 125 may be a physical computing system or may be a virtual computer instance (e.g., executing in a cloud computing platform). A care provider 101 may use the physician device 120 to access (e.g., via a browser application 122) a portal user interface 126 hosted by the portal 125. The portal user interface 126 itself provides users 102 (e.g., the care providers 101) with access to the care platform server 110.

The care platform server 110 includes various applications and data that allow a care provider 101 to create and manage a care plan for a patient 103. As shown, the care platform server 110 includes a care plan management application 111, policy information 112, patient information 113, care protocol templates 114, and care plans 115. The care plan management application 111 generates care plans 115 based on care protocol templates 114.

A care plan 115 may be created based on one or more care protocols, with each of the care protocols relating to a respective medical condition the patient has been diagnosed with. A care protocol is a set of tasks that a patient 103 follows to manage a certain condition, metrics that the care plan management application 111 monitors, objectives for the patient to meet, and the like. For instance, a care protocol may target recovery from a heart attack. Another care protocol may treat diabetes. Tasks associated with a care protocol may include steps such as exercising for a specified duration or taking medication at a certain time of day.

Further, each care plan protocol may be divided into different phases. The phases may represent different stages of care for a particular condition, e.g., a recovery phase, a maintenance phase, etc., where each phase may include a respective set of tasks for the patient to perform, observation metrics to monitor, observation thresholds to detect when the monitored metrics satisfy specified conditions. For example, a care protocol for weight management may include several phases. A patient 103 may begin the care protocol at a weight loss phase, where tasks may include performing strenuous exercises frequently, and where thresholds may specify further actions that the care plan management application 111 takes if the patient 103 loses X amount of weight or gains Y amount of weight. For example, if the metrics indicate that the patient 103 gained Y amount of weight after a period at which the patient 103 had a Z average activity level, the care plan management application 111 may instruct the patient 103 to watch an educational video in response. Continuing the example, if the patient 103 loses X amount of weight during a given period, the care plan management application 111 may transition the care protocol to a weight maintenance phase, where tasks may include exercises that assist the patient 103 in maintaining the weight.

Each care plan protocol may also include observation thresholds associated with monitored metrics and could further specify an action(s) to be taken responsive to an observation threshold being satisfied. The care platform server 110 may monitor the adherence of a patient 103 through various sensor devices 140 that can measure heart rate, weight, blood pressure, and the like. The care platform server 110 may take specified actions if one of the metrics crosses a corresponding threshold, e.g., if a patient 103 gains 1.5 pounds after a day, the platform server 110 may report the weight gain to the care provider 101.

To generate a care plan, a care provider 101 may configure care protocol templates 114 corresponding to medical conditions the patient 103 is diagnosed with. To do so, the care provider 101 (e.g., via the portal user interface 126) selects one or more care protocol templates 114 to associate with the patient 103. The care plan management application 111 copies the selected templates to a care plan 115, i.e., the care plan management application 114 populates the care plan 115 with tasks, triggers, and monitoring thresholds as specified by the selected care protocol templates 114. The portal user interface 126 may display the selected care protocol templates 114, where the care provider 101 may customize various facets of each selected template 114, such as tasks and thresholds. For example, the care provider 101 may customize a task instructing a patient to check blood pressure every morning. The care provider 101 may adjust the task so that the patient checks blood pressure twice a day. In addition, the care provider 101 may adjust thresholds associated with that task, such that the care platform server 110 alerts the care provider 101 if a threshold blood pressure is reached.

In one embodiment, each customization may be subject to comply with policy information 112 and such compliance may be enforced by the care plan management application 111 during the creation of the care plan. Policy information 112 may include various guidelines (e.g., set by a hospital, standards organization, insurance companies, etc.) that each care protocol must adhere to. For instance, the policy information 112 may specify milligram ranges for certain medications that may be assigned to a patient 103 in a care protocol. The care plan management application 111 may enforce such policy information 112 to ensure a care provider 101 configuring a care plan does not customize tasks beyond the bounds of the policy information 112.

The care plan management application 111 generates a care plan 115 for a patient 103 based on the customizations made by the care provider 101. In doing so, the care plan management application 111 identifies conflicting tasks across the selected care protocols. For example, a care protocol for high blood pressure may include a task instructing a patient to take 75 milligrams of aspirin three times a day, while another care protocol for a sprained ankle includes a task instructing the patient to take 100 milligrams of aspirin three times a day.

Generally, the patient information 113 represents patient-specific information describing a patient's medical history and treatment history. In one embodiment, the care plan management application 111 may generate the care plan 111 based on the patient information 113, in addition to customizations to care protocol templates 114 that the care provider 101 provides. Patient information 113 may include medications previously prescribed to the patient 103 and whether the medications had a beneficial or adverse effect towards the patient. In a case where a particular medication has had an adverse effect towards a patient 103, the care plan management application 111 may flag tasks associated with taking the medication to the care provider 101 configuring the care plan 115. In response, the care provider 101 may edit or remove the task.

Once generated, the care plan management application 110 may store the care plan 115 on the care platform server 110. Further, the care plan management application 110 transmits the care plan 115 to a mobile device 135 (e.g., to a patient care application 136 executing on the mobile device 135) of the patient 103. The patient 103 views the care plan (shown as care plan 137) on the mobile device through the patient care application 136. Doing so allows the patient 103 to understand tasks needed to adhere to the platform. Further, the care plan 137 is tightly coupled to the corresponding care plan 115. Any updates to either care plan 115 or 137 are synced with one another.

Moreover, the mobile device 135, upon receiving the care plan, could configure one or more monitoring devices to monitor one or more patient metrics as specified by the care plan. For example, the mobile device 135 could configure logic on a heart rate monitor device worn by the patient to monitor the patient's heart rate and to detect when the patient's heart rate exceeds a threshold number of beats per minute specified within the care plan. The heart rate monitor device, upon detecting that the threshold condition has been satisfied, could transmit an alert to the mobile device 135, which could in turn perform an action as specified by the care plan. For example, the mobile device 135, upon receiving the alert, could display a notification to the patient, informing the patient that his heart rate is elevated and instructing the patient to sit down and rest for a period of time. As another example, the mobile device 135 could generate a notification to the care plan management application 111, informing the care plan management application 111 that the patient's heart rate exceeds the threshold amount of beats per minute.

The patient care application 136 may display information related to the care plan 137, such as phases, tasks, and other information about conditions targeted for treatment by the care plan 137. When the patient 103 performs a task, the patient 103 records progress in the patient care application 136. The patient care application 136 relays this information to the care plan management application 111. Doing so allows the care provider 101 to monitor vitals of the patient 103 and adherence to the care plan. Further, depending on how the patient 103 responds to the care plan 137, the care plan management application 111 may adjust certain tasks.

In one embodiment, sensor devices 140 may interact with the patient care application 136 and assist the patient 103 in reporting body-related metrics to the care platform server 110. As shown, such sensor devices 140 may include a body sensor 141, a weighing scale 142, and a blood pressure cuff 143. Each of the sensor devices 140 may capture different body metrics of the patient 103. For example, when applied to the body of patient 103, the body sensor 141 captures biometric data (e.g., heart rate) in real-time. In addition, each of the sensor devices 140 may be configured to transmit the body-related metrics electronically to the patient care application 136 on the mobile device 135. In turn, the patient care application 136 sends the captured metrics to the care plan management application 111.

Figure 2:
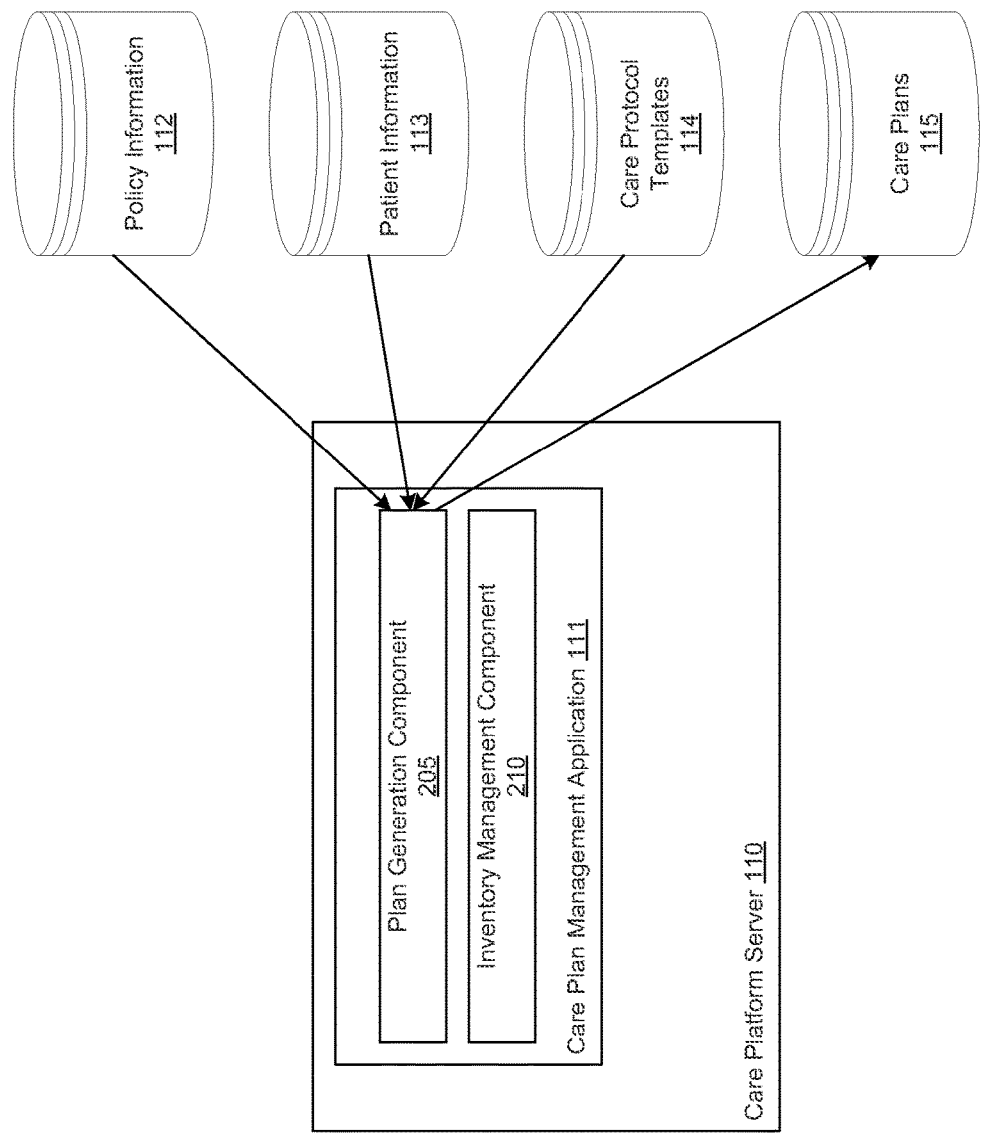
FIG. 2 further illustrates the care platform server described in FIG. 1, according to one embodiment.

FIG. 2 further illustrates the care platform server 115, according to one embodiment. As stated, the care plan management application 111 can be configured to generate a care plan 115 based on care protocol templates 114 selected by a care provider 101 and also based on policy information 112 and patient information 113.

As shown, the care plan management application 111 further includes a plan generation component 205 and an inventory management component 210. The plan generation component 205 receives selections of care protocol templates 114 from a care provider 101. The plan generation component may populate a care plan 115 with the phases, tasks, and thresholds specified in each of the care protocol templates 114 selected by the care provider 101.

Further, the plan generation component 205 may receive customizations to the tasks and thresholds of the care protocol templates 114. In addition, the care provider 101 may insert tasks and thresholds to any of the care protocol templates 114. The plan generation component 205 generates the care plan 115 based on the care protocol templates 114 and the care plans 115. In doing so, the plan generation component 205 ensures that any customizations to the care protocol templates 114 made by the care provider 101 comply with policy information 112.

Further, the plan generation component 205 resolves task and threshold information that conflict between different care protocol templates. In one embodiment, tasks and thresholds may be associated with conflict resolution rules such that in the event a conflict arises, the plan generation component 205 may resolve the conflicting tasks and thresholds based on such properties. The properties may be configured by care providers 103. For example, assume that a care protocol template 114 for a sprained ankle condition includes a task instructing a patient to take 80 milligrams of aspirin in the morning. Assume also that a care protocol template 114 for hypertension includes a task instructing a patient to take 150 milligrams of aspirin in the morning. A conflict resolution rule for the task of taking aspirin in the morning may specify that in the event of a conflict, the task instructing the patient to take the higher dosage should override. Thus, when a care provider 103 selects the care protocol templates 114 for a sprained ankle and hypertension for a patient, the plan generation component 114 reconciles the conflicting tasks by inserting the 150 milligrams of aspirin step in the care plan and disregarding the 80 milligrams of aspirin step. Another example of a conflict that may arise includes different care protocols instructing a patient to take two types of medication that should not be taken together. Conflict resolution rules for such tasks may include logic to avoid such combinations or raise a flag to the care provider 103 selecting the protocols. The care provider 103 may further customize the care protocol templates 114 in response.

In one embodiment, the plan generation component 205 may make additional customizations based on patient information 113. As stated, patient information 113 may include patient medical histories. Such histories may contain past treatment information for a given patient as well as information on the effectiveness of certain treatments to the patient. The patient information 113 may include other data such as allergies, past afflictions, etc. The plan generation component 205 may adjust tasks based on the patient information 113. For example, if the patient information 113 indicates that a patient is allergic to ibuprofen, the plan generation component 205 may substitute tasks mentioning ibuprofen with a similar medication. Alternatively, the plan generation component 205 may flag the task for further review by the care provider 101.

The inventory management component 210 maintains a store of sensor device configurations for patients registered with the care environment. The inventory management component 210 associates the patient care application 136 with the sensor devices 140. Further, the inventory management component 210 also associates a generated care plan with the patient care application 136 and sensor devices 140. Doing so ensures that the plan generation component 205 sends a generated care plan to the correct mobile device as well as configures the patient care application 136 and sensor devices 140 of the patient 103 with the relevant threshold information. Further, the inventory management component 210 maintains device integrity and ensures ease of use for the care provider 101. Once configured, the patient care application 136 allows the patient 103 to begin adhering to the individualized care plan.

FIG. 3 illustrates an example care protocol template 300, according to one embodiment. In one embodiment, a copy of the care protocol template 300 may be presented to a care provider 101 via a web browser interface. For example, the care provider 101 may access a portal server that presents the interface to the care provider 101. After entering a request to create a care plan, the interface may present the template 300 to the care provider 101. The care provider 101 enters information into and modifies a copy of each template 300. After doing so, the plan generation component 205 may create the care plan based on the templates and customizations.

As shown, the template 300 includes fields 305 and 310, where the care provider 101 may enter a name and an identifier of a patient to associate with a care plan. In addition, the template 300 includes a drop down menu 315 that allows the care provider 101 to select a particular care protocol. The drop down menu 315 may include a list of conditions for which a care protocol exists and is licensed in the care platform server. In this case, the care protocol shown is for high blood pressure.

After selecting a care protocol via the drop down menu 315, the interface may present tasks, thresholds, and metrics associated with the care protocol. For instance, the bottom half of the template 300 shows phase and task information associated with the care protocol for high blood pressure. The care provider 101 may modify a variety of tasks and other information associated with the care protocol. For example, the template 300 includes a field 320 that allows the care provider 101 to specify a duration for the care protocol to last.

In addition, the template 300 allows the care provider 101 to view phase information 325 associated with the protocol. The care provider 101 may select a phase to view using a drop down menu 330. After selecting a phase, the care provider 101 may view tasks associated with a particular phase, e.g., via a drop down menu 335. The template 300 may allow the care provider 101 to edit or remove selected tasks. The care provider 101 may also add tasks for phases and tasks to be across all phases as well.

Once the care provider 101 is finished customizing the selection, the care provider 101 may save the customizations. The plan management component 205 may allow the care provider 101 to add other care plan protocols until the care provider 101 has selected all the needed protocols for a patient.

FIG. 4 illustrates a task view 400 of the care protocol template 300, according to one embodiment. The task view 400 provides additional metrics that a care provider 101 may evaluate and edit for a given care protocol when creating a care plan to assign to a patient. As shown, the task view 400 includes fields 405, 410, and 415 that indicate a patient name, a patient ID, and a care protocol condition. The bottom half of task view 400 lists tasks associated with the selected care protocol. In this case, the tasks are associated with a "high blood pressure" care protocol.

As shown, the task view 400 lists the tasks in a column 420. Each task in the list 420 specifies an instruction that a patient should take, e.g., wearing a body sensor, taking blood pressure, and taking 60 milligrams of aspirin. Further, the task view 400 provides a column 425 specifying a frequency at which to perform a corresponding task, e.g., taking 60 milligrams of aspirin every morning.

The task view 400 also lists observation threshold sets 430 that a care provider 101 may configure. Each threshold set may correspond to a particular task metric in a care protocol, e.g., that is monitored though a sensor device associated with a patient. As shown, each threshold set 1 includes columns associated with a threshold type, a value, a warning level, associated symptoms reported by a patient (e.g., via the patient care application 136), and alert type. Each threshold is associated with a tier-based warning level that indicates a severity of the threshold. For example, a tier 1 warning level may be of a mild severity, while in contrast, a tier 3 warning level may be of a high severity. If a patient reaches a particular observation threshold, the care platform server may take a specified action, such as recording the event to a medical chart of a patient, notifying a care provider 101, etc. The care plan management application 111 may also prompt the patient 103 to report any symptoms (e.g., via the patient care application 136). Based on rules associated with the threshold triggers, the care plan management application 111 may elevate the warning level to the next tier in response to reported symptoms being noted with the observed metrics. For example, if the care plan management application 111 detects, based on a specified threshold, that the heart rate of the patient is over a value X, the care plan management application 111 may instruct the patient to rest and also prompt the patient to enter symptoms. If particular symptoms (specified in the threshold) are present, the care plan management application 111 may elevate to the next tier in response. However, if no (or other) symptoms are present, then the care plan management application 111 may continuously monitor the heart rate of the patient for a given time period to determine whether the heart rate drops within an acceptable range, and act accordingly after the end of the time period.

Consider threshold set 1 shown in the task view 400. Threshold set 1 corresponds to thresholds related to monitoring weight over a weekly basis. If the care platform server detects that a patient associated with the care plan has gained 2.5 kilograms over a weeklong period, the care platform server may record the information on the patient's medical chart.

A care provider 101 may add, delete, or modify observation thresholds as necessary. Further, the care provider 101 may add or delete threshold sets for associated tasks, as well.

Figure 5:
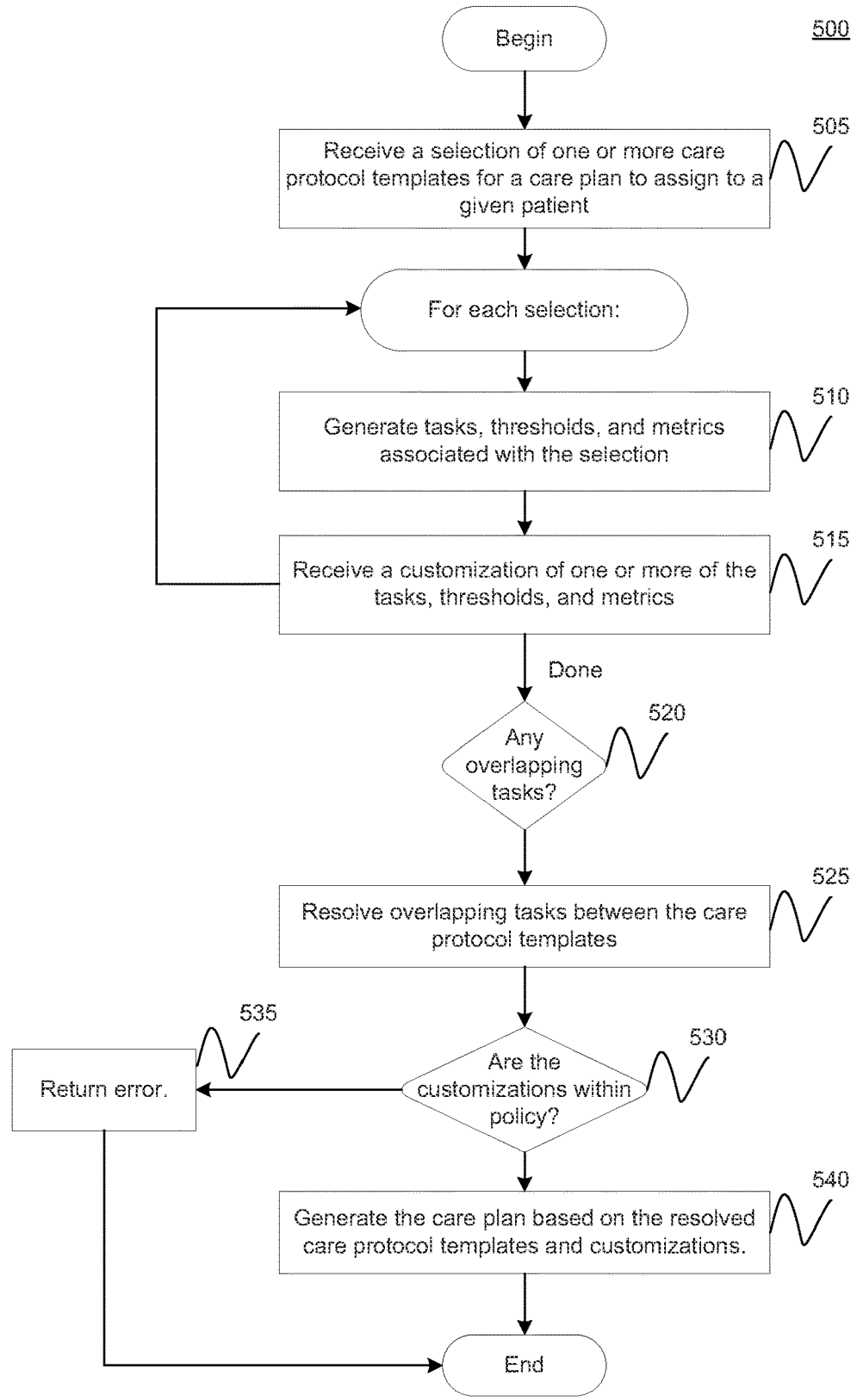
FIG. 5 illustrates a method for generating a care plan, according to one embodiment.

FIG. 5 illustrates a method 500 for generating a health care plan that may be customized for an individual, according to one embodiment. Assume that a care provider (e.g., a physician, clinician, medical professional, etc.) has sent a request to the care platform server 110 to create a care plan for a patient and that in response, the care plan management application 111 has sent a number of selectable care protocol templates to the care provider.

Method 500 begins at step 505, where the plan generation component 205 receives a selection of one or more care protocol templates. For example, assume that the plan generation component 205 receives a selection of a care protocol template for diabetes and a care protocol template for high blood pressure.

For each selection, the plan generation component 205 generates tasks, thresholds, and metrics associated with the selection (at step 510). The plan generation component 205 populates the care plan with the tasks, thresholds, and metrics. Continuing the previous example, the plan generation component 205 may populate the care plan with tasks, thresholds, and metrics for both of the selected care plans. The care provider may view the tasks, thresholds, and metrics via a portal interface and customize each, e.g., by adding, editing, or removing tasks. For example, assume that the care plan protocol for diabetes includes a task instructing the patient to record weight every morning. The care provider may customize the protocol by removing that task or editing the task to be less periodic. At step 515, the plan generation component 205 receives the customizations made by the care provider.

After receiving the customizations to each of the care protocol templates, the plan generation component 205 determines whether any tasks or thresholds conflict with one another (at step 520). If so, then at step 525, the plan generation component 205 resolves the conflicting tasks between the care protocol templates based on associated conflict resolution rules between the tasks. Continuing the previous example, assume that the care plan protocol for diabetes includes a task for taking insulin seven times a day to control the glucose level of the patient. Further assume that the care plan protocol for high blood pressure includes a task for taking beta blockers three times a day to lower the blood pressure of the patient. Both tasks may include conflict resolution rules specifying that insulin and beta blockers should not be taken in the same care plan. In such a case, the plan generation component 205 may act according to logic specified the conflict resolution rules, e.g., raising a flag to the care provider for review, adding the overriding task to the care plan and disregarding the other, etc.

At step 530, the plan generation component 205 determines whether the customizations provided by the care provider comply with policy information 112. Doing so ensures that any customizations to certain tasks are within bounds established by the policy information 112. If not, then at step 535, the plan generation component 205 may flag noncompliant tasks to the care provider for review. If so, then the plan generation component 205 generates the care plan based on the resolved care protocol templates and customizations. The plan generation component 205 associates the care plan with the patient and sends the care plan to the mobile device of the patient.

Figure 6:
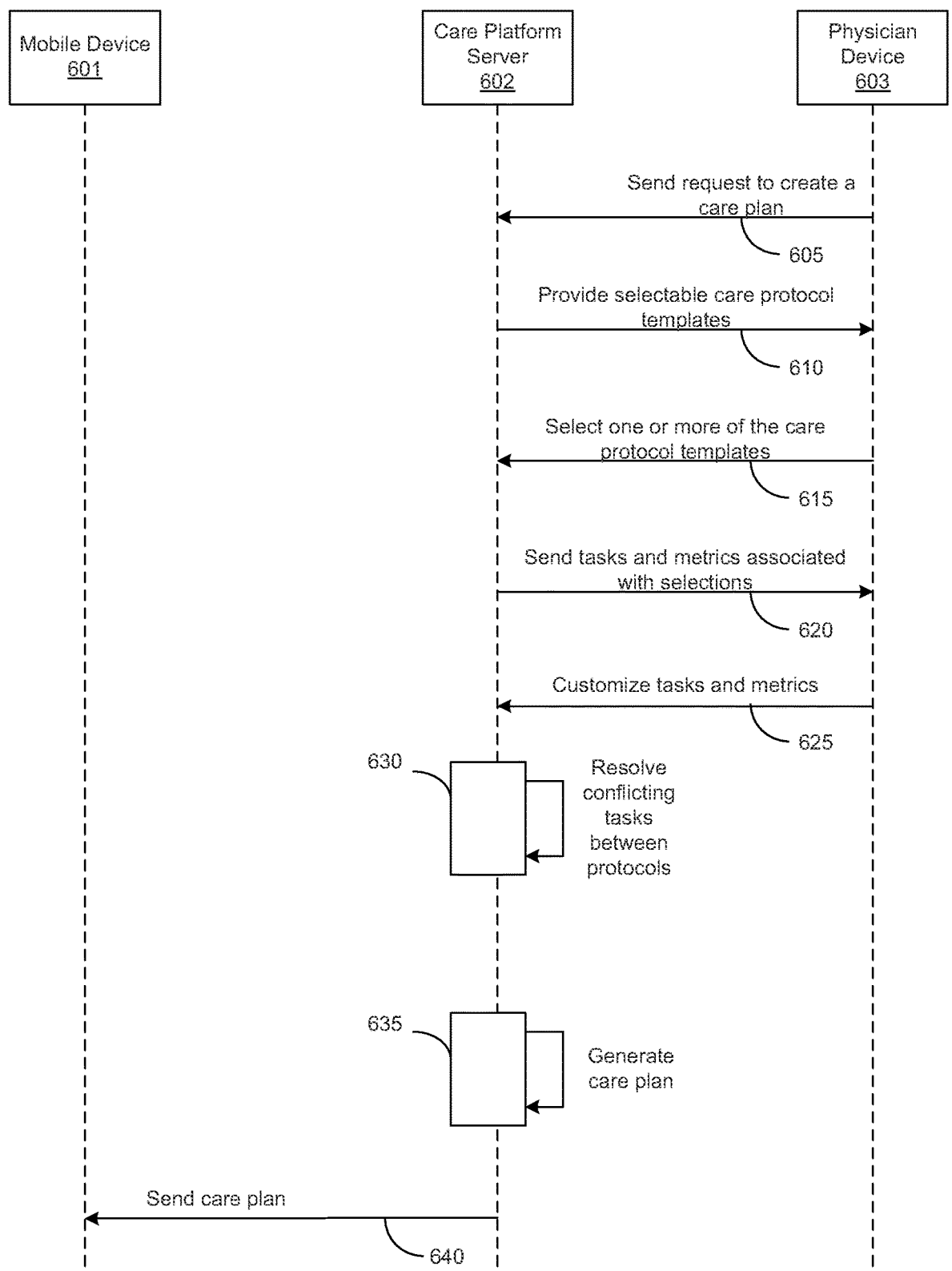
FIG. 6 illustrates a sequence for creating a care plan based on care protocol templates to associate with a patient, according to one embodiment.

FIG. 6 illustrates a sequence 600 for generating a health care plan that may be customized for an individual, according to one embodiment. Specifically, the sequence 600 demonstrates interactions between a mobile device 601, a care platform server 602, and a physician device 603 in creating a care plan.

At 605, the physician device 603 sends a request to create a care plan. In response, at step 610, the care platform server 602 sends selectable care protocol templates to the physician device 603. At 615, the physician device 603 sends a selection of one or more of the care protocol templates to the care platform server 602. The care platform server 602 populates the care plan with tasks and other metrics associated with each of the selected care protocol templates. At 620, the care platform server 602 sends the tasks and metrics to the physician device for customization.

At 625, the physician device 603 sends customizations for the tasks and metrics to the care platform server 602. At 630, the care platform server 602 resolves conflicting tasks between the selected care protocols and customizations. At 635, the care platform server 602 generates a care plan based on the selected protocols and customizations. Once generated, at 640, the care platform sever 602 sends the generated care plan to the mobile device 601.

Figure 7:
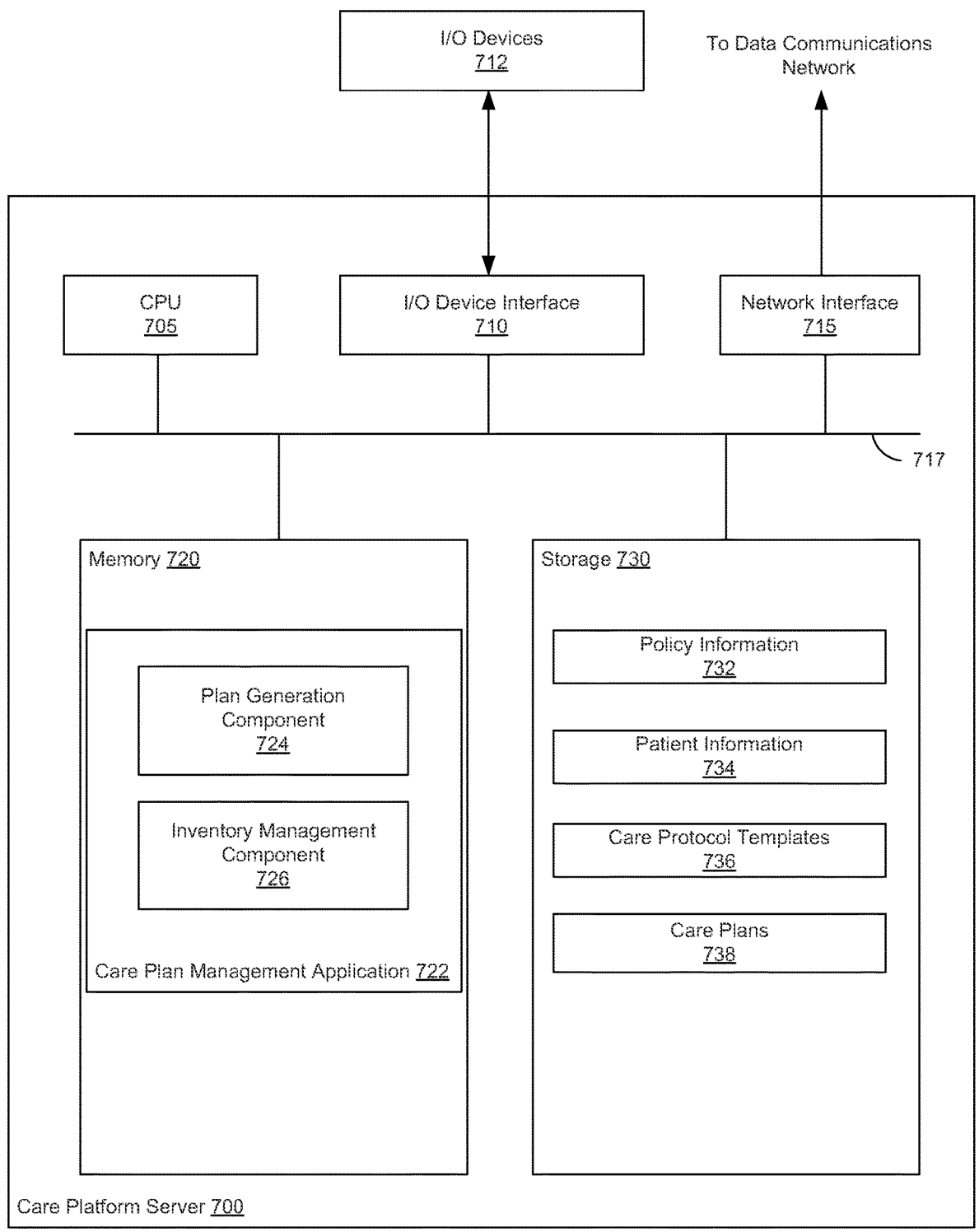
FIG. 7 illustrates a care platform server configured to generate a care plan, according to one embodiment.

FIG. 7 illustrates a care platform server 700 configured to generate a care plan that may be customized for an individual, according to one embodiment. As shown, the care platform server 700 includes, without limitation, a central processing unit (CPU) 705, a network interface 715, a memory 720, and storage 730, each connected to a bus 717. The care platform server may also include an I/O device interface 710 connecting I/O devices 712 (e.g., keyboard, display and mouse devices) to the care platform server 700. Further, in context of this disclosure, the computing elements shown in the care platform server 700 may correspond to a physical computing system (e.g., a system in a data center) or may be a virtual computing instance executing within a computing cloud.

CPU 705 retrieves and executes programming instructions stored in memory 720 as well as stores and retrieves application data residing in the storage 730. The bus 717 is used to transmit programming instructions and application data between CPU 705, I/O devices interface 710, storage 730, network interface 717, and memory 720. Note, CPU 705 is included to be representative of a single CPU, multiple CPUs, a single CPU having multiple processing cores, and the like. Memory 720 is generally included to be representative of a random access memory. Storage 730 may be a disk drive storage device. Although shown as a single unit, storage 730 may be a combination of fixed and/or removable storage devices, such as fixed disc drives, removable memory cards, or optical storage, network attached storage (NAS), or a storage area-network (SAN).

Illustratively, memory 720 includes a care plan management application 722. And storage 730 includes policy information 732, patient information 734, care protocol templates 736, and care plans 738. The care plan management application 722 further includes a plan generation component 724 and an inventory management component 726. The plan generation component 724 creates a care plan 738 based on a received selection of care protocol templates 736, received customizations of the selected templates 736, policy information 732, and patient information 734.

Each care protocol template 736 provides a set of tasks, thresholds, and other metrics targeted towards treating a certain condition (e.g., diabetes, heart issues, etc.). Although care protocol templates 736 are general in nature, a care provider may modify the care protocol template 736 to be specific to a given patient (e.g., by adding, editing, and removing tasks). The plan generation component 724 may resolve conflicts between overlapping tasks and thresholds based on conflict resolution rules associated with each task and threshold.

The inventory management component 726 associates sensor devices issued by a care provider (e.g., body sensors, weight scales, etc.) with patients. Further, the inventory management component 726 associates a care plan with a mobile device application of the patient to ensure that the plan generation component 205 sends the care plan to the correct mobile device.

Policy information 732 includes various guidelines (e.g., set by a hospital, standards organization, insurance companies, etc.) that each care protocol assigned by a care provider should adhere to. For example, the policy information 732 may specify acceptable bounds of medication to instruct a patient to take. The plan generation component 724 may enforce the policy information 732 when generating a care plan 738, e.g., by raising a flag for a care provider to review in the event that the care provider customizes a care protocol in a way that violates the policy information 732.

Patient information 734 includes patient medical histories and charts. Such histories and charts may provide treatment information that the plan generation component 724 may use to identify effective and detrimental treatments (e.g., medications, exercises, etc.) applied to a patient in the past. Once identified, the plan generation component 724 may modify a care plan 738 based on the identified information.

One embodiment of the present disclosure is implemented as a program product for use with a computer system. The program(s) of the program product defines functions of the embodiments (including the methods described herein) and can be contained on a variety of computer-readable storage media. Examples of computer-readable storage media include (i) non-writable storage media (e.g., read-only memory devices within a computer such as CD-ROM or DVD-ROM disks readable by an optical media drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present disclosure, are embodiments of the present disclosure. Other examples media include communications media through which information is conveyed to a computer, such as through a computer or telephone network, including wireless communications networks.

In general, the routines executed to implement the embodiments of the present disclosure may be part of an operating system or a specific application, component, program, module, object, or sequence of instructions. The computer program of the present disclosure is comprised typically of a multitude of instructions that will be translated by the native computer into a machine-readable format and hence executable instructions. Also, programs are comprised of variables and data structures that either reside locally to the program or are found in memory or on storage devices. In addition, various programs described herein may be identified based upon the application for which they are implemented in a specific embodiment of the disclosure. However, it should be appreciated that any particular program nomenclature that follows is used merely for convenience, and thus the present disclosure should not be limited to use solely in any specific application identified and/or implied by such nomenclature.

As described, embodiments herein provide techniques for generating a health care plan that may be customized for an individual. Advantageously, the care plans that the care platform generates may be tailored to a specific individual. Doing so allows a care provider to provide a more detailed and effective approach to treating a patient's condition than a care plan that consists of generalized tasks. Further, because the care plan may be tied to mobile and sensor devices of the patient, the care platform may monitor the progress of the patient's adherence to the care plan, allowing for further customization of the care plan as necessary.

While the foregoing is directed to embodiments of the present disclosure, other and further embodiments of the disclosure may be devised without departing from the basic scope thereof, and the scope thereof is determined by the claims that follow.

What is claimed is:

1. A method for generating a care plan describing a treatment regimen for a patient, the method comprising:
   receiving, via a processor at a care platform server, a selection of a first care protocol template and a second care protocol template to assign to the patient, wherein each of the first and second care protocol templates is associated with a respective treatment regimen for a corresponding medical condition and wherein at least one of the selected first or second care protocol templates comprises a first conflict resolution rule;
   generating, using the processor at the care platform server, a care plan based on the first and second care protocol templates, wherein the care plan includes a plurality of items related to the treatment regimens;
   applying a received customization to at least one of the plurality of items in the care plan;
   identifying, using the processor at the care platform server, a first patient task associated with the first care protocol template that conflicts with a second patient task associated with the second care protocol template, and in response:
      parsing, using the processor at the care platform server, the first and second care protocol templates to identify the first conflict resolution rule, wherein the first conflict resolution rule is pre-defined in the respective template prior to the identifying the conflict;
      resolving the conflict based on the first conflict resolution rule, wherein resolving the conflict comprises:
         identifying logic in the first conflict resolution rule relating to resolving the conflict, and generating a third patient task using the logic; and
         including the third patient task in the care plan;

associating the care plan with a client device for the patient, at the care platform server, using an inventory management component of the care platform server;

transmitting the care plan to the client device, wherein the care plan specifies a configuration for one or more sensor devices, at least one threshold condition and at least one treatment plan;

configuring, at the client device upon receiving the care plan, the one or more sensor devices to collect biometric data for monitoring the patient, the configuration comprising transmitting the threshold condition from the client device to at least one of the sensor devices;

receiving, at the client device of the patient, biometric data collected using the one or more sensor devices;

transmitting, from the client device to the care platform server, the collected biometric data; and determining, at the client device of the patient, that the collected biometric data satisfies at least one threshold condition specified in the care plan, and in response initiating at least one treatment plan specified in the care plan and corresponding to the satisfied at least one threshold condition, the at least one treatment plan comprising a treatment task for the patient to perform.

2. The method of claim 1, further comprising, prior to identifying the conflict, determining whether the received customizations comply with a policy specifying acceptable ranges of customization for items in the selected one or more care protocol templates.

3. The method of claim 2, further comprising, upon determining that one of the customizations does not comply with the policy, disallowing the customization such that the customization is not applied to any items within the care plan.

4. The method of claim 1, further comprising:
retrieving historical patient information describing one or more previous treatment regimens for the patient;
determining one or more historical items from the one or more previous treatment regimens that are related to a first item in the plurality of items;
determining one or more modifications to first item, based on a determined measure of success for one or more related historical items in the one or more previous treatment regimens for the patient; and
performing the determined modification on the first item within the care plan.

5. The method of claim 1, wherein the plurality of items are organized into phases of treatment for the patient, each phase including conditions which, when satisfied, result in a transition between a currently active phase and another one of the phases.

6. The method of claim 1, wherein the plurality of items comprises at least one of tasks, observation metrics, and thresholds.

7. The method of claim 6, wherein the tasks are actions to be performed by the patient according to a schedule specified in the care plan, wherein the observation metrics specify biometric data to monitor from the patient, and wherein the thresholds are conditions for the observation metrics that, when a care platform system detects the conditions are satisfied, cause the care platform system to perform an action in response.

8. A computer-readable storage medium storing instructions, which, when executed on a processor, performs an operation for generating a care plan that describes an overall treatment regimen for a patient, the operation comprising:
receiving, via a processor at a care platform server, a selection of a first care protocol template and a second care protocol template to assign to the patient, wherein each of the first and second care protocol templates is associated with a respective treatment regimen for a corresponding medical condition and wherein at least one of the selected first or second care protocol templates comprises a first conflict resolution rule;

generating, using the processor at the care platform server, a care plan based on the first and second care protocol templates, wherein the care plan includes a plurality of items related to the treatment regimens;

applying a received customization to at least one of the plurality of items in the care plan;

identifying, using the processor at the care platform server, a first patient task associated with the first care protocol template that conflicts with a second patient task associated with the second care protocol template, and in response:
parsing, using the processor at the care platform server, the first and second care protocol templates to identify the first conflict resolution rule, wherein the first conflict resolution rule is pre-defined in the respective template prior to the identifying the conflict;
resolving the conflict based on the first conflict resolution rule, wherein resolving the conflict comprises:
identifying logic in the first conflict resolution rule relating to resolving the conflict, and generating a third patient task using the logic; and
including the third patient task in the care plan;

associating the care plan with a client device for the patient, at the care platform server, using an inventory management component of the care platform server;

transmitting the care plan to the client device, wherein the care plan specifies a configuration for one or more sensor devices, at least one threshold condition and at least one treatment plan; configuring, at the client device upon receiving the care plan, the one or more sensor devices to collect biometric data for monitoring the patient, the configuration comprising transmitting the threshold condition from the client device to at least one of the sensor devices;

receiving, at the client device of the patient, biometric data collected using the one or more sensor devices;

transmitting, from the client device to the care platform server, the collected biometric data; and determining, at the client device of the patient, that the collected biometric data satisfies at least one threshold condition specified in the care plan, and in response initiating at least one treatment plan specified in the care plan and corresponding to the satisfied at least one threshold condition, the at least one treatment plan comprising a treatment task for the patient to perform.

9. A system, comprising:
one or more processors; and
one or more memories storing one or more application programs configured to perform an operation for generating a care plan that describes an overall treatment regimen for a patient, the operation comprising:
receiving, via a processor at a care platform server, a selection of a first care protocol template and a second care protocol template to assign to the patient, wherein each of the first and second care protocol templates is associated with a respective treatment regimen for a corresponding medical condition and wherein at least one of the selected first or second care protocol templates comprises a first conflict resolution rule;

generating, using the processor at the care platform server, a care plan based on the first and second care protocol templates, wherein the care plan includes a plurality of items related to the treatment regimens;

applying a received customization to at least one of the plurality of items in the care plan;

identifying, using the processor at the care platform server, a first patient task associated with the first care protocol template that conflicts with a second patient task associated with the second care protocol template, and in response:

parsing, using the processor at the care platform server, the first and second care protocol templates to identify the first conflict resolution rule, wherein the first conflict resolution rule is pre-defined in the respective template prior to the identifying the conflict;

resolving the conflict based on the first conflict resolution rule, wherein resolving the conflict comprises:

identifying logic in the first conflict resolution rule relating to resolving the conflict, and generating a third patient task using the logic; and including the third patient task in the care plan;

associating the care plan with a client device for the patient, at the care platform server, using an inventory management component of the care platform server;

transmitting the care plan to the client device, wherein the care plan specifies a configuration for one or more sensor devices, at least one threshold condition and at least one treatment plan; configuring, at the client device upon receiving the care plan, the one or more sensor devices to collect biometric data for monitoring the patient, the configuration comprising transmitting the threshold condition from the client device to at least one of the sensor devices;

receiving, at the client device of the patient, biometric data collected using the one or more sensor devices;

transmitting, from the client device to the care platform server, the collected biometric data; and determining, at the client device of the patient, that the collected biometric data satisfies at least one threshold condition specified in the care plan, and in response initiating at least one treatment plan specified in the care plan and corresponding to the satisfied at least one threshold condition, the at least one treatment plan comprising a treatment task for the patient to perform.

10. The system of claim 9, wherein the operation further comprises, prior to identifying the conflict, determining whether the received customizations comply with a policy specifying acceptable ranges of customization for items in the selected one or more care protocol templates.

11. The system of claim 10, wherein the operation further comprises, upon determining that one of the customizations does not comply with the policy, disallowing the customization such that the customization is not applied to any items within the care plan.

12. The system of claim 9, wherein the operation further comprises:

retrieving historical patient information describing one or more previous treatment regimens for the patient;

determining one or more historical items from the one or more previous treatment regimens that are related to a first item in the plurality of items;

determining one or more modifications to first item, based on a determined measure of success for one or more related historical items in the one or more previous treatment regimens for the patient; and performing the determined modification on the first item within the care plan.

13. The system of claim 9, wherein the plurality of items are organized into phases of treatment for the patient, each phase including conditions which, when satisfied, result in a transition between a currently active phase and another one of the phases.

14. The system of claim 9, wherein the plurality of items comprises at least one of tasks, observation metrics, and thresholds, wherein the tasks are actions to be performed by the patient according to a schedule specified in the care plan, wherein the observation metrics specify biometric data to monitor from the patient, and wherein the thresholds are conditions for the observation metrics that, when a care platform system detects the conditions are satisfied, cause the care platform system to perform an action in response.

15. The method of claim 1, wherein the first patient task and the second patient task specify a common task to be performed by the patient according to a first schedule and a second schedule, respectively, and wherein resolving the conflict based on the first conflict resolution rule further comprises:

determining a timing schedule for performing the common task that resolves the conflict; and updating the care plan to replace the first patient task and the second patient task with the third patient task, wherein the third patient task specifies to perform the common task according to the determined timing schedule.

16. The method of claim 1, wherein the one or more sensor devices are configured to collect the biometric data and transmit the biometric data to the client device using a first data communications network, and wherein the client device is configured to transmit the biometric data to the care platform server using a second data communications network.

17. The method of claim 1, further comprising:

determining the one or more sensor devices by accessing, using identifying information for the patient, an inventory management component that associates sensor devices issued by a care provider with patients of the care provider; and associating, by the inventory management component, the care plan with the client device and the one or more sensor devices of the patient.

18. The method of claim 1, wherein the plurality of items comprises at least one task for the patient to complete and a schedule specifying timing information by which the at least one task must be completed by the patient in order for the patient to be considered in compliance with the care plan.

19. The method of claim 1, wherein the treatment task is initiated by the client device and comprises initiating an alert to a care provider relating to the patient.

* * * * *